United States Patent
Arsenault, Jr. et al.

(10) Patent No.: US 9,279,754 B1
(45) Date of Patent: Mar. 8, 2016

(54) METHOD AND APPARATUS FOR TESTING A CABLE

(71) Applicant: EMC Corporation, Hopkinton, MA (US)

(72) Inventors: Michael Arsenault, Jr., North Dartmouth, MA (US); Mickey S. Felton, Sterling, MA (US)

(73) Assignee: EMC CORPORATION, Hopkinton, MA (US)

( * ) Notice: Subject to any disclaimer, the term of this patent is extended or adjusted under 35 U.S.C. 154(b) by 3 days.

(21) Appl. No.: 14/488,072

(22) Filed: Sep. 16, 2014

(51) Int. Cl.
*G01N 3/08* (2006.01)
*G01R 31/08* (2006.01)
*G01N 33/20* (2006.01)

(52) U.S. Cl.
CPC .................. *G01N 3/08* (2013.01); *G01N 33/20* (2013.01); *G01R 31/083* (2013.01)

(58) Field of Classification Search
CPC .......... G01R 31/083; G01R 33/20; G01R 3/08
USPC ....................... 73/828, 830, 862.392, 862.393
See application file for complete search history.

(56) References Cited

U.S. PATENT DOCUMENTS

| | | | | | |
|---|---|---|---|---|---|
| 4,023,154 | A | * | 5/1977 | Comeaux | G01R 31/083 324/524 |
| 4,718,168 | A | * | 1/1988 | Kerr | E21B 47/04 324/206 |
| 5,012,680 | A | * | 5/1991 | Castagnoli | G01G 19/08 73/862.393 |
| 5,731,528 | A | * | 3/1998 | Yamazaki | G01L 5/042 73/828 |
| 6,215,315 | B1 | * | 4/2001 | Maejima | G11B 15/6835 324/539 |

* cited by examiner

*Primary Examiner* — Max Noori
(74) *Attorney, Agent, or Firm* — Day Pitney LLP

(57) ABSTRACT

Method and apparatus for testing a cable call for extending the cable along a route having at least one curved portion, applying tension in an axial direction to the sheath of the extended cable so as to elongate the sheath, perturbing the tensioned cable in an axial direction and determining whether the perturbations to the tensioned cable have caused any structural distortions in the cable.

20 Claims, 6 Drawing Sheets

METHOD AND APPARATUS FOR TESTING A CABLE

BACKGROUND OF THE INVENTION

1. Field of the Invention

The present invention relates to communication cables, and in particular relates to a methods for simulating the effects of routing a copper cable and determining any structural distortions and/or deterioration resulting therefrom.

2. Description of the Related Art

Network and communication equipment is often physically arranged according to specific configuration requirements. Communication cables, that carry signals to and from such equipment, may be required to be routed along one or more relatively sharp curves, according to the configuration and constraints of the setting, such as the shape and size of a chassis or drawer. Such routing can put tension on the outside sheath of the cable, and result in distortion and degradation of the various wires within the cable. One type of distortion is referred to as "micro-pistoning."

FIG. 1, is schematic illustration depicting aspects of micro-pistoning. In FIG. 1, a cable 100, having a sheath 101 and two sub-cables 102, 104, each in turn having two conductors, is bent into a U-type shape. As shown, the bending has caused the end of sub-cable 102 to protrude upwards relative to the end of sub-cable 104 on the left side, and conversely, the end of sub-cable 104 protrudes upwards relative to the end of sub-cable 102 on the right side. If, for example, the bend occurred when one of the ends was soldered, or otherwise fixed to equipment, it can be seen that such relative movement can alter or damage the structural integrity of such a connection, and possibly cause signal transport discontinuity.

Testing of cables according to known standards such as the SFF 8417 standard (Small Form Factor Committee "Multi Conductor Cable Flex Cycle Test Procedure") involves determining whether particular points of a tensioned cable break when flexed angularly back and forth over a set number of repetitions. Such tests do not provide a good guide as to whether a cable will perform adequately when routed as described above, and in particular, do not provide any indication of any possible micro-pistoning behavior of the cable.

What is needed is a test that provides useful information for indicating whether a communication cable will perform adequately under prevailing routing conditions, and in particular provides information indicating whether micro-pistoning or other structural distortions have occurred, which hitherto have not been subject to rigorous testing.

SUMMARY OF THE INVENTION

According to one aspect of the invention, a method of testing a cable is provided. The method includes extending the cable along a route having at least one curved portion, applying tension in an axial direction to the sheath of the extended cable so as to elongate the sheath, perturbing the tensioned cable in an axial direction and determining whether the perturbations to the tensioned cable have caused any structural distortions in the cable.

According to another aspect of the invention, an apparatus for testing a cable is provided. The apparatus includes a motor, a cable holder coupled to the motor adapted to hold a first section of the cable, curving means for curving a second section of the cable routed from the cable holder and tensioning means for applying tension in an axial direction to the sheath of the cable in the vicinity of the curving means; wherein the motor is operative to move the cable via the cable holder in an axial direction while the tensioning means applies tension to the sheath of the cable.

In one embodiment, a method of testing a cable having a sheath and at least two conductors disposed within the sheath is provided. The method includes: a) extending the cable along a route having at least one curved portion; b) applying tension in an axial direction to the sheath of the extended cable so as to elongate the sheath; c) perturbing the tensioned cable in an axial direction; and d) determining whether the perturbations to the tensioned cable have caused any structural distortions in the cable.

In another embodiment, an apparatus for testing a cable having a sheath and at least two conductors is provided. The apparatus includes a motor; a cable holder coupled to the motor adapted to hold a first section of the cable; apparatus for curving a second section of the cable routed from the cable holder; and apparatus for applying tension in an axial direction to the sheath of the cable in the vicinity of the curving apparatus; wherein the motor is operative to move the cable via the cable holder in an axial direction while the tensioning apparatus applies tension to the sheath of the cable.

These and other features and advantages of the present invention will become apparent in light of the drawings and detailed description provided below.

BRIEF DESCRIPTION OF THE DRAWINGS

The features and advantages of the invention are apparent from the following description taken in conjunction with the accompanying drawings in which.

DETAILED DESCRIPTION OF THE INVENTION

According to embodiments of the present invention, a method and apparatus for testing a cable is provided indicating whether a communication cable will perform adequately under prevailing routing conditions, and determines whether the cable is likely to undergo micro-pistoning or other structural distortions under typical routing conditions. According to embodiments of the method, a cable is routed with curved sections that simulate typical routing conditions and then the sheath of the cable is subjected to tension tending to elongate the cable with respect to the conductors therein. In this condition, the cable is perturbed by linear (in the axial direction) motions for one or more cycles, simulating pressures that cables are often subject to when, for example, drawers of equipment chassis are moved or pivoted. At the end of the perturbation cycles, the cable may be reoriented and re-subjected to tension and perturbation. This may be repeated until all orientations have been tested. The cable may then be repositioned longitudinally and further sections of the cable may then be tested. Upon completion of the testing of the entire cable, it is determined whether the perturbations have caused any structural distortions in the cable.

As used herein, the term "cable" generally refers to a channel or group of channels for conducting electrical signals having an insulating external layer, or sheath, surrounding one, or preferably, two or more conductors. Generally, a "sub-cable" is a unit that may be included in a cable that itself contains two or more conductors. For example, a cable may include two sub-cables, each having two conductors, and thus may comprise four conductors altogether. In general, a cable typically includes some multiple of two (2×) conductors.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present.

Figure 1:
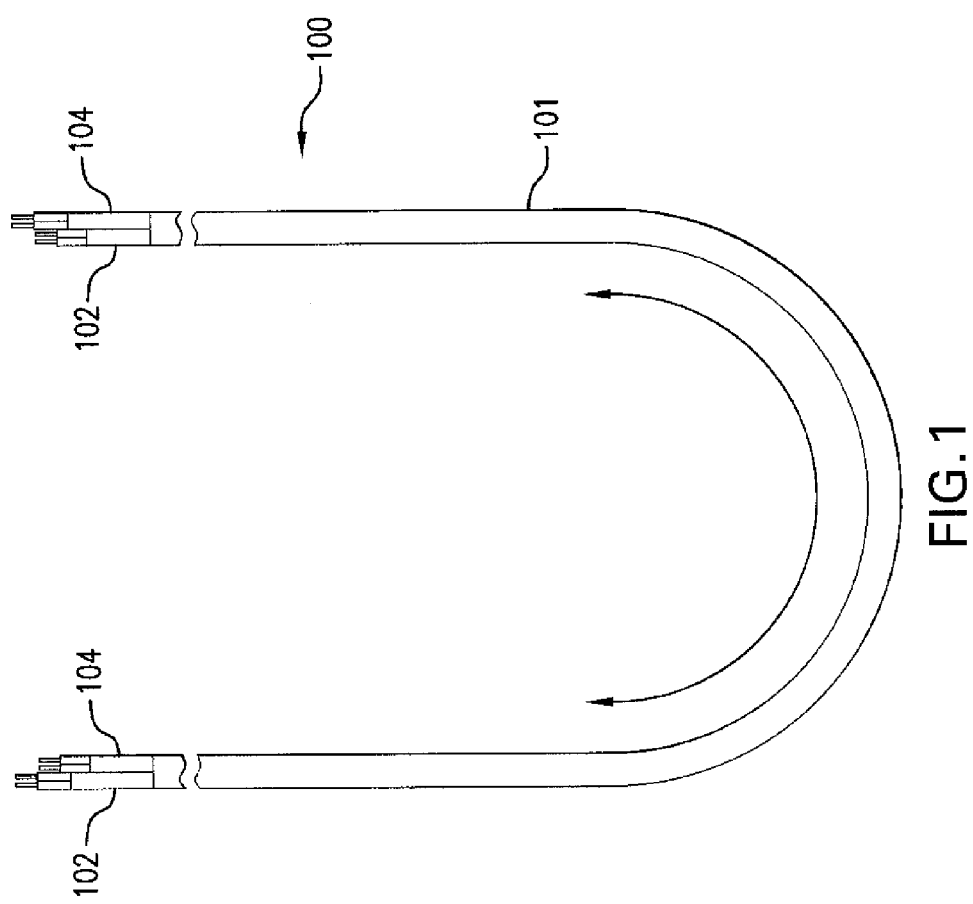
FIG. 1 is a schematic illustration of micro-pistoning.
Figure 2:
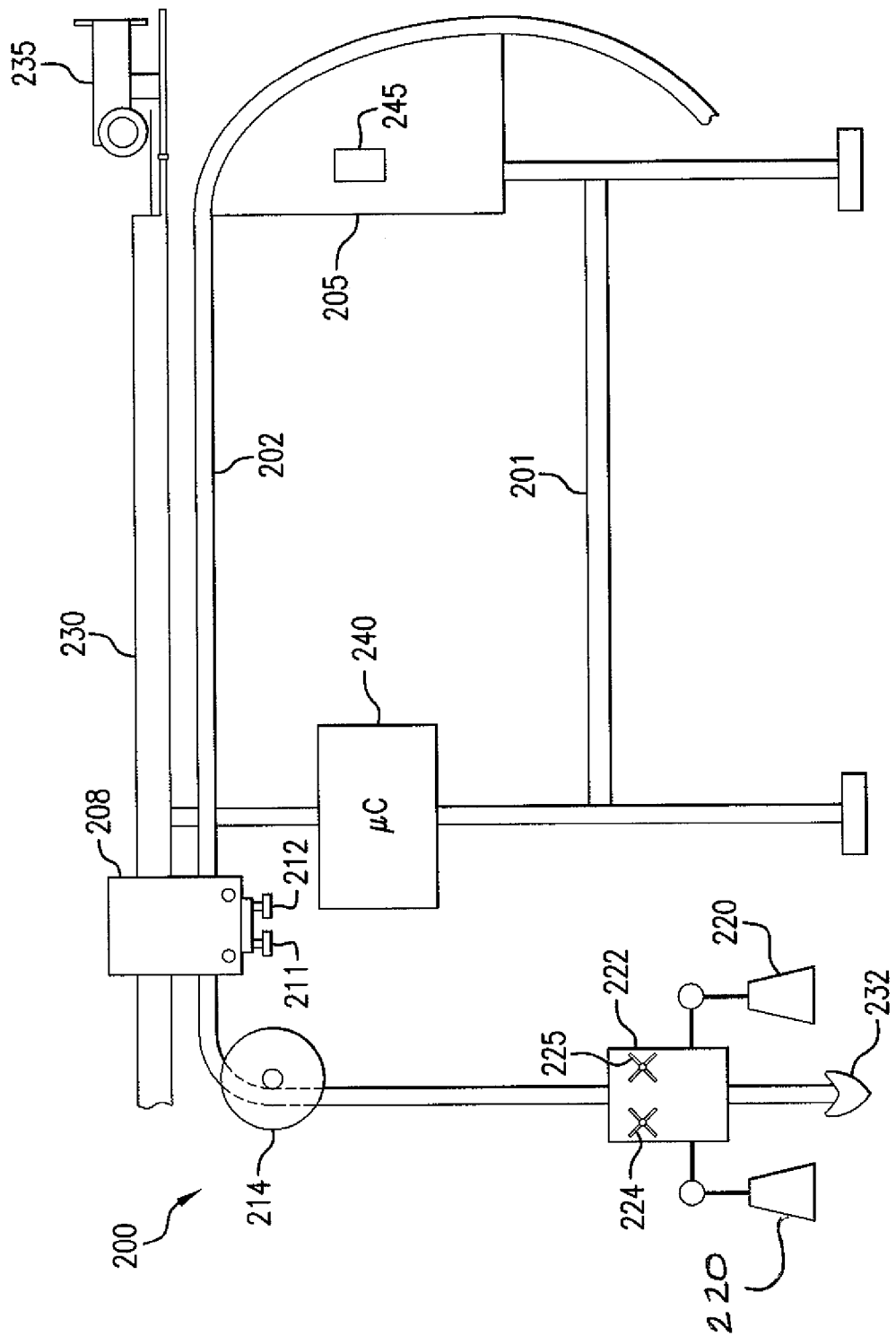
FIG. 2 is a schematic front view of an apparatus for testing a cable according to an exemplary embodiment of the present invention.
Figure 3:
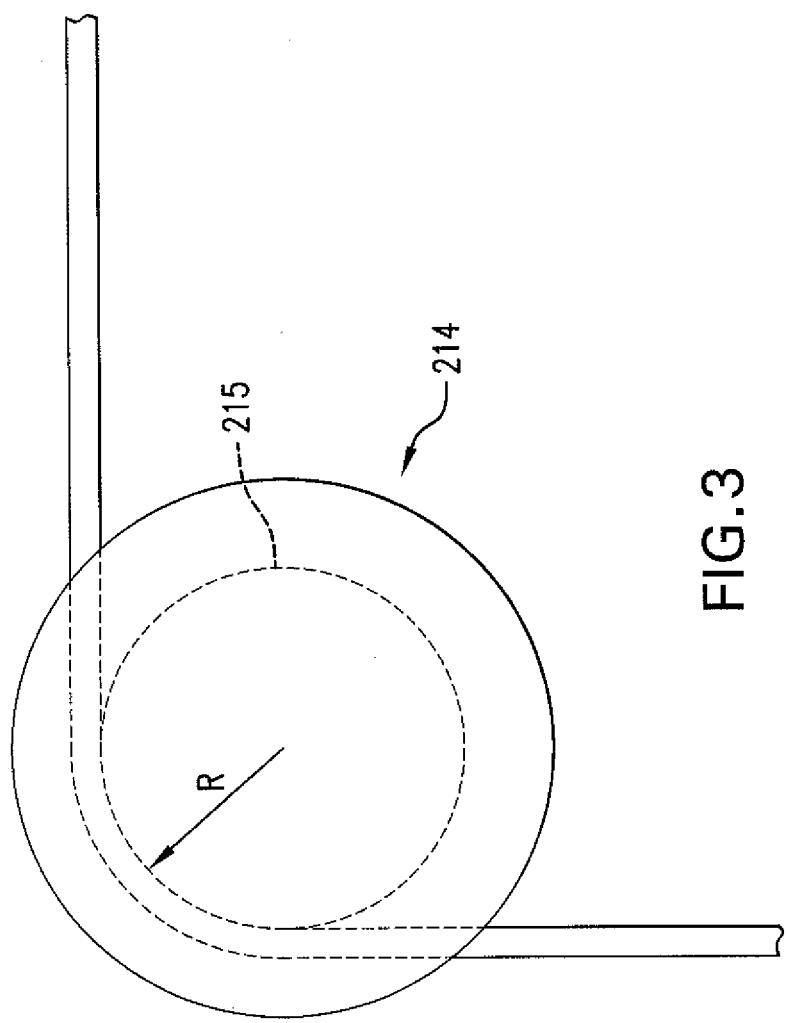
FIG. 3 is a schematic expanded view of the routing of a cable around a curve.

Referring to FIG. 2, an apparatus 200 for testing a cable according to an embodiment of the present invention is shown. Apparatus 200 includes a modular frame structure 201 adapted to support the other components. All components described below are coupled to frame structure 201 unless otherwise stated. Apparatus 200 includes travel guide 205 that holds a cable 202 to be tested having a sheath surrounding two or more sub-cable or conductors (not shown in FIG. 2). From the travel guide 205, the cable 202 is routed downstream (towards the left) to a cable holder 208. The cable holder 208 is adapted to firmly attach to the sheath of the cable 202 while allowing the conductors within the cable a degree of movement and free play. This may be accomplished, for example, by means of clamps 211, 212 which apply enough pressure to the sheath to keep it from moving while not affecting the movement of the conductors within. From the cable holder 208, cable 202 is routed around a pulley 214. The radius of pulley may be selected so as to simulate an expected turn radius of cables employed in the field. FIG. 3 illustrates the radius of curvature (R) of the curved portion of the cable 202 as it turns on the inner track 215 of pulley 214. In particular, as can be discerned, the radius (R) of the curved portion approximately matches the radius of the inner track 215 of pulley 214. A typical range of radius (R) found to simulate field conditions is 1 to 3 inches, although other values may be used. It is noted that while FIG. 2 shows cable 202 being routed so as to have one curved portion at pulley 214, cable 202 may be routed over further curved sections using pulleys, diverters, or any other devices or features known in the art. The purpose in each case is to simulate particular routing conditions of interest to determine if a cable will suffer distortion or damage when subject to such conditions.

The remaining length of the cable 202 is routed downwards along the left side of the apparatus 200. According to one embodiment of the invention, weights 220 (meaning one or more weights, but the plural "weights" is used herein) are coupled to the sheath on the distal side of the pulley 214 to simulate tension forces that tend to elongate the sheath and possibly induce micro-pistoning or other structural distortions. The magnitude of weights 220 is determined so as to provide an appropriate amount of force to simulate the forces cables are typically subjected to in practice. It is found that range of 25,000 to 45,000 psi is generally suitable, although other values may be used. Accordingly, with knowledge of the geometry of the cable 202, in particular the number and size of the conductors in the cable 202, an appropriate value for the weights 220 may be calculated. The weights 220 may be coupled directly to a second cable holder 222 with clamps 224, 225 similarly adapted to hold the sheath of cable 202 while permitting the conductors within the cable 202 a degree of motion.

Although use of weights (the force of gravity) is illustrated as the mechanism for applying tension to the sheath of the cable 202, this is only one convenient method for simulating tensioning forces and other mechanisms, forces and actuators may be used in other embodiments. For example, in some embodiments rather than having the distal end of the cable 202 hang downwards under tension from gravity, the distal end of the cable 202 may be routed upwards and subject to tension using electrical actuators such as solenoids.

The first cable holder 208 is coupled to a linear guide 230. As will be described in more detail below in FIGS. 4, 5, a motor 235, such as a stepper motor may induce the cable holder 208 to move horizontally forwards (to the left) or backwards (to the right) in accordance with instructions generated by a microcontroller 240. Parameters for the testing may be entered into the microcontroller via a control panel 245. The microcontroller 240 may include a processor, firmware and/or software for executing instructions stored in or on computer-readable storage media such as but not limited to optical disks, hard disks, CD-ROMs, and magnetic-optical disks, or read-only memories (ROMs), random access memories (RAMS), erasable ROMs (EPROMs), electrically erasable ROMs (EEPROMs), magnetic or optical cards, or any type of non-transitory media suitable for storing computer-readable instructions. The motion of the cable holder 208 is constrained by the linear guide 230 from moving laterally ensuring that the cable holder 208, and in turn cable 202, can be moved smoothly. A vertical guide (not shown) may also be included to constrain the motion of second cable holder 222. During initial testing (subjecting the cable 202 to motion and tension) the distal end of the cable 202 may be encased in a protective cover 232. After initial testing, the distal end of the cable may be fixed or coupled to electrical testing equipment as will be discussed below.

Figure 4:
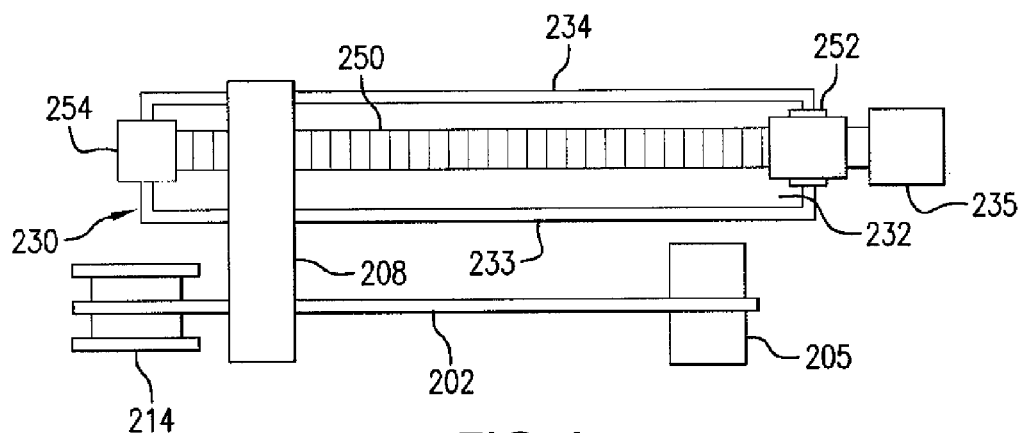
FIG. 4 is a schematic top view of the apparatus for testing a cable of FIG. 1.

FIG. 4 is a schematic top view of the exemplary embodiment of the apparatus 200 of FIG. 2. The cable 202 is shown routed from the travel guide 205 through cable holder 208 over pulley 214. In this view, the exemplary mechanism by which the cable holder 208 is moved is more clearly indicated. As shown, cable holder 208 is placed snuggly in groove 232 of the linear guide 230 between railings 233, 234. The cable holder 208 includes a hollow portion through which a belt 250 passes through while being securely fastened to the holder (this is more clearly shown in FIG. 5 below). The belt 250 may be grooved to prevent slippage and to ensure accurate movement and control. The belt 250 runs from a driver pulley 252 operatively coupled to the motor 235 on the upstream side, through cable holder 208 to return pulley 254. Pulleys 252, 254 may include corresponding grooved surfaces for operatively coupling with grooves of the belt 250.

Figure 5:
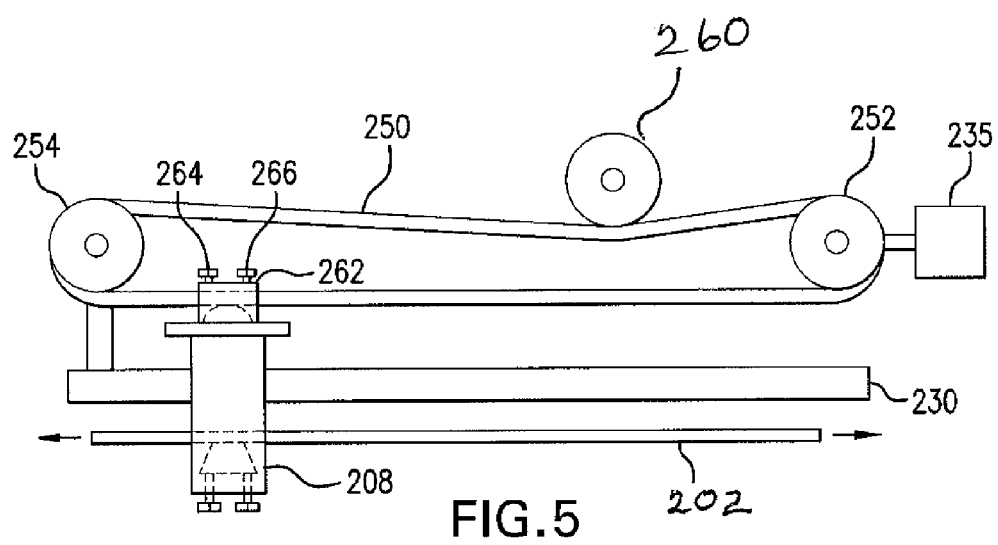
FIG. 5 is a schematic front view of a movement mechanism of the apparatus of FIG. 1.

FIG. 5 is a frontal view showing further details of the exemplary movement mechanism of apparatus 200 shown in FIG. 4. The full circuit of belt 250 is shown, running between pulleys 252, 254. A tensioner pulley 260 is included to prevent the belt from running slack and thus ensures that the belt transmits enough force to move cable holder according to the speed programmed via the microcontroller or set manually. The cable holder 208 includes a hollowed top section 262 through which the belt 250 passes. The belt 250 may be securely and removably coupled to the cable holder 208 by means of clamps 264, 266 which may be used to press the belt against an appropriate pliable, non-damaging material such as foam rubber.

The exemplary apparatus 200 discussed above is designed to perform the task of subjecting the cable 202 to perturbations that simulate typical field conditions. Cables that do not suffer physical distortion or damage during such tests are deemed suitable for routing applications.

Figure 6:
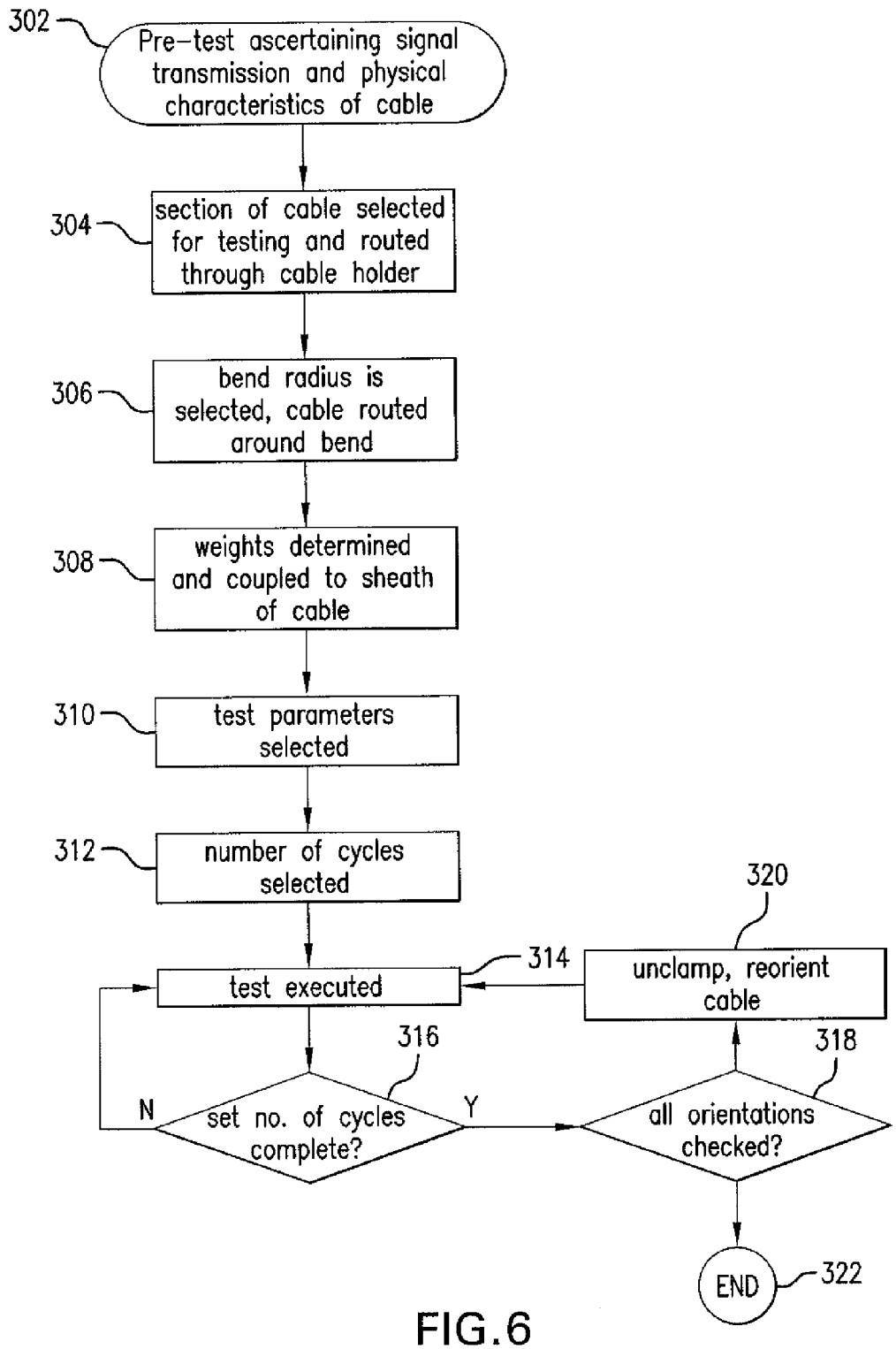
FIG. 6 is a flow chart of an exemplary method of testing a cable.

FIG. 6 is a flow chart of an exemplary method for testing a cable. In an initial step 302, the pre-testing characteristics of a cable 202 to be tested are ascertained to form a basis for post-test comparison. The characteristics ascertained may include signal transmission quality, determined by a running test signals from a signal generator at a first end of the cable to a monitoring device such as a scope at the other end which would indicate any changes in the signal due to the properties of the cable. Physical characteristics for example, cable cross-section parameters, which may be compared to manufacturer specifications, are also ascertained, with any deviation from specifications noted for post-test comparison. Once the initial characteristics of the cable 202 are determined, in step 304, a section of the cable 202 is selected for testing and the cable is routed through the apparatus, and suitably coupled to the cable holder 208. In step 306, a bend radius for pulley 214 is selected to simulate routing conditions in field, and a suitably sized pulley (or other suitable device for providing the bend radius) is fitted onto the apparatus and the cable is routed over the pulley, providing a curved section of cable with the corresponding selected bend radius. In the following step 308, the magnitude of the weights 220 is calculated based on the physical characteristics of the cable 202, in particular the number and size of the conductors, and weights of the calculated amount are coupled to the sheath of the cable 202 via second cable holder 222.

At this point the test, or perturbation, parameters are selected by a tester based on the physical properties of the cable, the field conditions simulated and rules of thumb developed during testing. In first test parameter selection step 310, the speed and distance at which the cable holder 208 is moved by motor 235 via belt 250 is selected. Suitable speeds typically range from [insert speed] and distance typically range from 0.15 m to 0.35 m. Generally, the perturbing movement is a back and forth motion over the entire distance simulating repeated pulses of tension as the cable and weights are pulled upwards and pushed down. The number of repetitions of the perturbation, or number of cycles, which is an index of the total stress to which the cable is subjected, is selected in step 312. The parameters may be entered pre-programmed or entered into the microcontroller 240 via control panel 245. After selection of the parameters, in step 314, a test is executed and the perturbation of the cable begins. In step 316, a check is run to determine whether the preset number of cycles has been completed. If so, the test proceeds to step 318, if not the test cycles back to step 314. In step 318, a further check is run to see if all orientations of the cable have been checked. If so, the test of the selected cable section ends in step 322; if not the method proceeds to step 320 in which the cable 202 is unclamped from the apparatus, reoriented or rotated about its axis, re-clamped and then tested again in step 314.

In accordance with the test, a section of cable is subjected to cycles of perturbations in all orientations, and is thus subject to a substantial degree of stress which should amply simulate the stresses routed cables undergo in the field. The test may be repeated for other sections of the cable, and in fact, the entire length of cable may be tested in the same manner by repeatedly coupling different sections of the cable to the apparatus.

Figure 7:
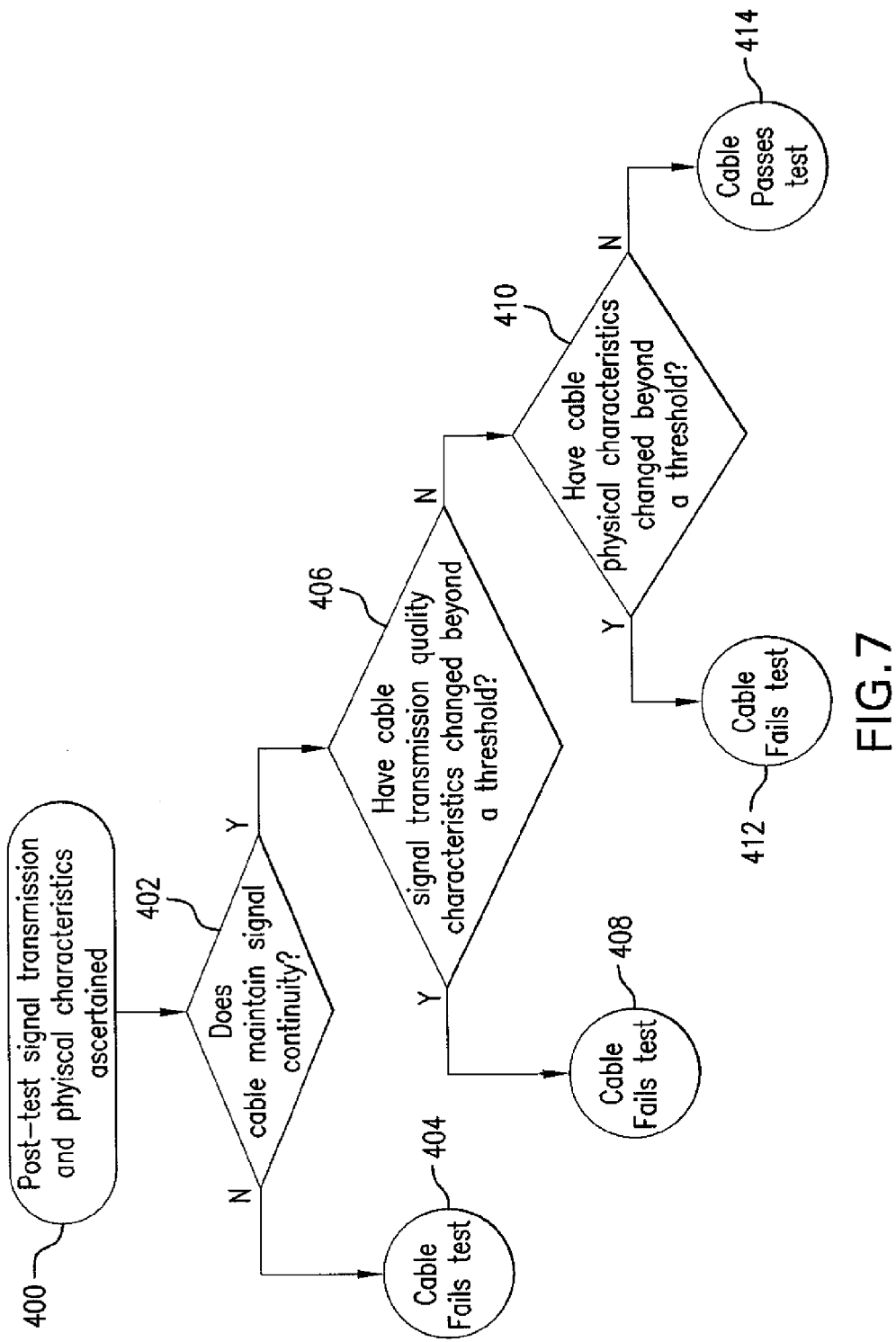
FIG. 7 is a flow chart of an exemplary method of post-test cable fitness determination.

FIG. 7 is a flow chart of a method of post-test cable fitness determination according to an exemplary embodiment of the present invention. In step 400, post-test cable characteristics are ascertained in the same manner as obtained pre-test in step 302 of the method shown in FIG. 6. That is, signal transmission quality is again determined by a running the same test signals from a signal generator at a first end of the cable to a monitoring device such as a scope at the other end and the same physical characteristics ascertained before are measured. In step 402, it is determined whether the cable is still able to maintain signal continuity. If so, the process proceeds to step 406, if not, it is determined that the cable has failed the test and the method ends in step 404. In step 406, a comparison between post-test and pre-test signal transmission quality characteristics is made, and it is determined whether the cable signal transmission quality characteristics have altered due to the stresses applied by the test. The signal transmission quality may be measured by running signals from a test signal generator at one of the cable to a monitor device or scope on the other end. Alternatively, one end of the cable can be coupled to a test signal generator and the other end soldered or otherwise electrically coupled to equipment and the end equipment may be monitored.

The tester may choose to ignore de-minimus of minor changes, so that the comparison may determine whether the difference between the pre-test and post-test signal transmission quality characteristics is greater than a minimal threshold, indicating that the test has caused enough distortion of the characteristics to be of concern. If the signal transmission quality characteristics have changed beyond a threshold, it is determined that the cable has failed the test and the method ends at step 408. Alternatively, if the signal transmission quality characteristics have not changed beyond the threshold, at step 410, a further comparison is made between pre-test and post-test physical characteristics, and it is determined whether the physical characteristics have changed beyond the threshold. This may be determined by examining physical changes to the ends of the cable, and to changes in the cross-section at one or more point along the length of the cable. It is noted in this regard, that in the course of the test, the examination of the actual cable tested may damage the cable or otherwise affect its characteristics; however, the purpose of the test is not so much to determine the suitability of a particular cable for routing, but to determine whether cable manufactured according to the same specification as the tested cable are fit candidates, and can be reliably used in the field. If it is found in step 410 that the physical characteristics have changed beyond the threshold, it is determined that the cable has failed the test and the method ends in step 412. Alternatively, if it is found in step 410 that the physical characteristics have not changed beyond the threshold, it is determined in step 414 that the cable passes the test, and that cables manufactured according to the specification of the tested cable are good candidates for typical routing applications.

In alternative embodiments, at least some steps of the post-testing cable fitness determination can be performed during the testing. For example, it is possible to perform signal continuity determination by monitoring a signal transmitted through the cable during the testing of the cable as described above.

The present invention is not to be limited in scope by the specific embodiments described herein. Indeed, various modifications of the present invention, in addition to those described herein, will be apparent to those of ordinary skill in the art from the foregoing description and accompanying drawings. Thus, such modifications are intended to fall within the scope of the invention. Further, although aspects of the present invention have been described herein in the context of a particular implementation in a particular environment for a particular purpose, those of ordinary skill in the art will recognize that its usefulness is not limited thereto and that the present invention can be beneficially implemented in any number of environments for any number of purposes.

What is claimed is:

1. A method of testing a cable having a sheath and at least two conductors disposed within the sheath, the method comprising:
   a) extending the cable along a route having at least one curved portion;
   b) applying tension in an axial direction to the sheath of the extended cable so as to elongate the sheath;
   c) perturbing the tensioned cable in an axial direction; and
   d) determining whether the perturbations to the tensioned cable have caused any structural distortions in the cable.

2. The method of claim 1, wherein the step of applying tension to the cable comprises attaching at least one weight to the sheath of the cable.

3. The method of claim 2, further comprising determining the at least one weight so as to apply between 20,000 psi and 40,000 psi to the sheath.

4. The method of claim 1, wherein the step of perturbing the cable comprises moving the cable axially backwards and forwards through a range of four (4) to fifteen (15) inches.

5. The method of claim 1, wherein the curved portion has a radius of curvature in a range of 1 to 4 inches.

6. The method of claim 1, further comprising:
   determining a number of cycles for perturbing the tensioned cable in an axial direction.

7. The method of claim 1, further comprising:
   reorienting the cable about its axis; and
   repeating steps (a) through (c).

8. The method of claim 1, wherein the step of determining whether the perturbations to the tensioned cable have caused any structural distortions in the cable comprises determining whether the cable is able to maintain signal continuity when a signal is transmitted through the at least two conductors.

9. The method of claim 1, further comprising:
   determining at least one of a signal transmission quality characteristic and physical characteristic of the cable prior to performing steps (a) through (d); and
   in step (d), determining whether the signal transmission quality characteristics and physical characteristics of the cable have changed; and
   comparing a degree of change to a performance standard.

10. The method of claim 1, wherein an entire length of the cable is tested.

11. The method of claim 1, wherein tension is applied to the sheath while allowing the at least two conductors to move.

12. An apparatus for testing a cable having a sheath and at least two conductors comprising:
    a motor;
    a cable holder coupled to the motor adapted to hold a first section of the cable;
    apparatus for curving a second section of the cable routed from the cable holder; and
    apparatus for applying tension in an axial direction to the sheath of the cable in the vicinity of the curving apparatus;
    wherein the motor is operative to move the cable via the cable holder in an axial direction while the tensioning apparatus applies tension to the sheath of the cable.

13. The apparatus of claim 12, further comprising:
    a microcontroller coupled to the motor adapted to set a speed, direction and distance in which the motor moves the cable holder.

14. The apparatus of claim 12, wherein the curving apparatus comprises a pulley of a selected radius.

15. The apparatus of claim 14, wherein the pulley has a radius in a range of 1 to 4 inches.

16. The apparatus of claim 12, wherein the tensioning apparatus comprises at least one weight coupled to the sheath of the cable.

17. The apparatus of claim 16, wherein the at least one weight is set so as to apply between 20,000 psi and 40,000 psi to the sheath.

18. The apparatus of claim 12, further comprising:
    a linear guide adapted to securely receive the cable holder;
    a belt coupled to the motor and to the cable holder disposed in the linear guide; and
    a set of pulleys moveably coupled to the belt.

19. The apparatus of claim 18, wherein the belt is grooved and the set of pulleys include corresponding grooved surfaces for cooperating with the belt.

20. The apparatus of claim 12, further comprising:
    at least one monitoring device adapted to monitor electrical signal transmitted through the cable.